United States Patent [19]

Maeda et al.

[11] Patent Number: 4,806,626
[45] Date of Patent: Feb. 21, 1989

[54] α-AMYLASE INHIBITOR

[75] Inventors: Koji Maeda, Tokorozawa; Osamu Oka, Kawagoe, both of Japan

[73] Assignees: Nisshin Flour Milling Co., Ltd.; Oriental Yeast Co., Ltd., both of Japan

[21] Appl. No.: 63,697

[22] Filed: Jun. 15, 1987

Related U.S. Application Data

[63] Continuation of Ser. No. 918,520, Oct. 14, 1986, abandoned, which is a continuation of Ser. No. 578,189, Feb. 8, 1984, abandoned, which is a continuation of Ser. No. 347,261, Feb. 9, 1982, abandoned.

[30] Foreign Application Priority Data

Feb. 10, 1981 [JP] Japan ................... 56-18549

[51] Int. Cl.$^4$ .................. C07K 3/02; C07K 15/10; C12P 21/00; C12Q 1/40
[52] U.S. Cl. .................... 530/375; 435/22; 435/68; 514/2
[58] Field of Search ............... 435/68, 70, 71, 184, 435/204, 810, 22; 514/2, 12; 530/375

[56] References Cited

PUBLICATIONS

O'Donnell et al; Biochim. Biophys. ACTA 422: 159 (1976).
Silano et al, "Inhibition of Amylases from Different Origins by Albumins from the Wheat Kernel", Biochim. Biophys. Acta 391: 170 (1975).

*Primary Examiner*—James Martinell
*Attorney, Agent, or Firm*—Abelman Frayne Rezac & Schwab

[57] ABSTRACT

New α-amylase inhibitor from wheat (WAI-53). The inhibitor is characterized especially by having molecular weight of 24,000 as determined by gel filtration, giving a single band at an electrophoretic mobility of 0.53 on polyacrylamide gel electrophoresis according to the Davis Disc Electrophoresis Method and producing saturation curves of WAI-53 with human salivary alpha-amylase and with human pancreatic alpha-amylase with a ratio of the amount of WAI-53 required to produce 50% inhibition of human salivary α-amylase to that of human pancreatic amylase above 1:250. The alpha-amylase inhibitor is used for quantitative analysis of alpha-amylase isozymes in body fluid.

4 Claims, 2 Drawing Sheets

α-AMYLASE INHIBITOR

This application is a continuation of application Ser. No. 06/918,520 filed Oct. 14, 1986, now abandoned, which is a continuation of application Ser. No. 06/578,189, filed Feb. 8, 1984, now abandoned, which is a continuation of Ser. No. 06/347,261, filed Feb. 9, 1982, now abandoned.

BACKGROUND ART

The present invention relates to a new α-amylase inhibitor from wheat (WAI-53) a method for the preparation thereof, and a method of quantitative analysis of α-amylase isozymes in body fluid using the said α-amylase inhibitor of the present invention.

α-amylase is a hydrolytic enzyme widely distributing in living organisms. Human α-amylases are mainly produced by salivary gland and pancreas and are known to vary considerably in quantity in certain diseases such as pancreatitis, parasynanche, liver diseases, cancer and the like. Accordingly it is desired, for the precise diagnosis of such diseases, to have a method of quantitative analysis not only of total α-amylase in serum but also of each of the α-amylase isozymes produced by salivary gland and pancreas.

In clinical laboratories, electrophoretic method is currently used for the discriminative assay of human α-amylase isozymes. However, the method is too complicated to permit easy and quick assay of clinical samples, and requires skill for the evaluation of the results.

To overcome these difficulties, a process had been developed by O'Donnell et al wherein an α-amylase inhibitor from wheat is utilized. The process is, however, not really satisfactory and not quite of practical use. [Clin. Chem., 23, 23, 560-566 (1977)].

SUMMARY OF THE INVENTION

It has now been found that those difficulties and defects are overcome by the process of present invention described in detail below.

The present invention is related to an α-amylase inhibitor from wheat flour (WAI-53). It also provides a process for the preparation thereof wherein a new α-amylase inhibitor (WAI-53) contained in aqueous extract from wheat grains or wheat flour is separated and purified by means of ethanol precipitation, heat denaturation, anionic ion exchange chromatography, gel filtration chromatography, and cationic ion exchange chromatography in sequence. The present invention further provides a method of discriminative analysis of α-amylase isozymes in human body fluid whereby the present new α-amylase inhibitor (WAI-53) is used.

Wheat grains or wheat flour of any variety or of any grade may be used as a raw material for the preparation of the α-amylase inhibitor of the present invention, including hard wheat, Japanese wheat, soft wheat, durum wheat or strong flour, medium flour, soft flour and the like. Albumin fraction of any wheat grains contains the desired α-amylase inhibitor, though the content may vary.

Figure 1:
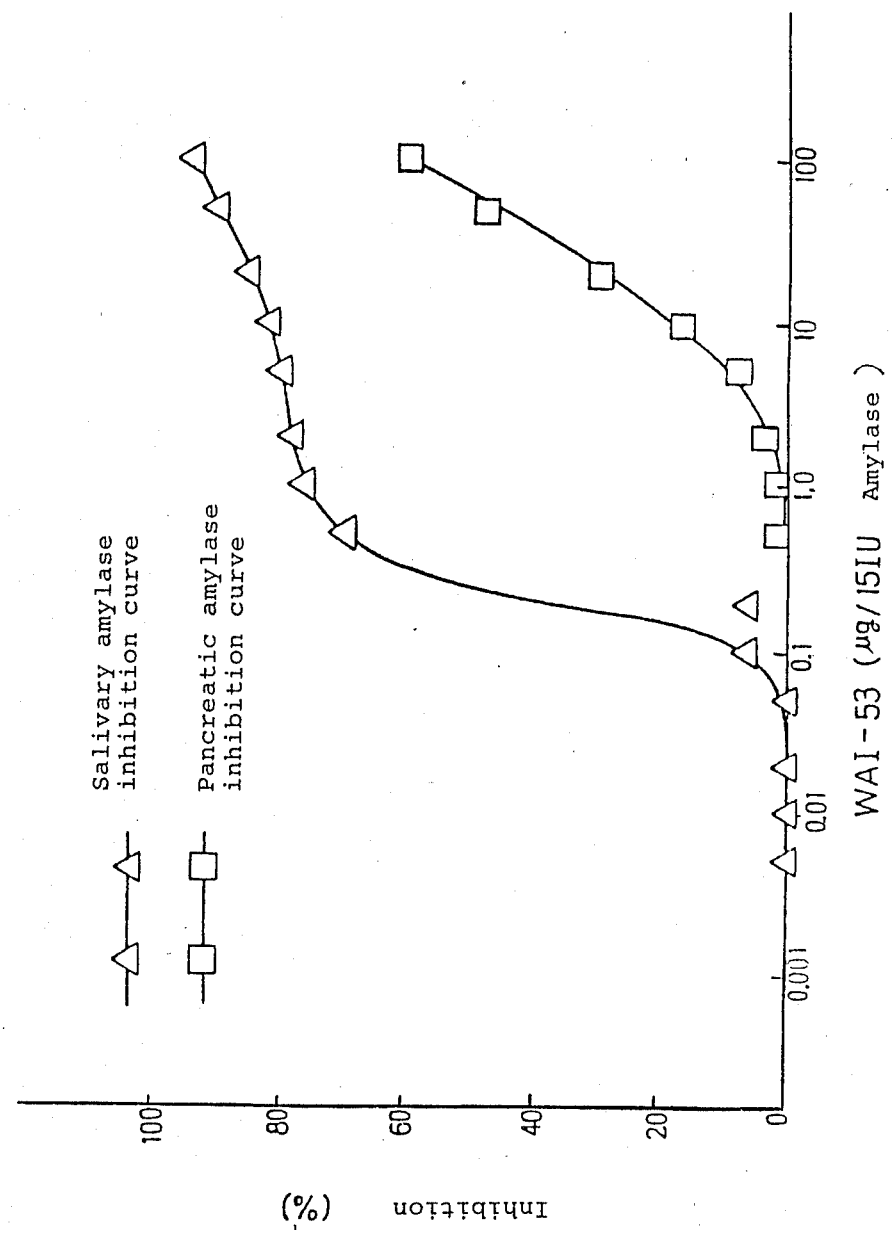
FIG. 1 is the plot of % inhibition of salivary and pancreatic α-amylases by the present α-amylase inhibitor (WAI-53) against the concentration thereof.

The new α-amylase inhibitor of the present invention (WAI-53) may be prepared by the process described below.

DESCRIPTION OF THE PREFERRED EMBODIMENTS

Wheat or wheat flour was stirred with 3-10 times of water, or preferably deionized water for 1-5 hours at room temperature to effect extraction of WAI-53. Insoluble materials in the aqueous mixture were separated by a conventional method such as centrifugation, decantation, filtration and the like to give a supernatant.

The supernatant was heated under reduced pressure or at an atmospheric pressure. Heating at 50°-70° C. for 10 min. to one hour is usually sufficient. Heating at 70° C. for 30 minutes is preferred. If desired, the heated solution may be futher subjected to centrifugation, decantation, filtration or the like to give a clear supernatant.

The heat-treated extract (or clear supernatant) was treated with a water-miscible organic solvent such as aqueous acetone, ethanol or methanol (to give a final organic solvent concentration of 40-70% V/V) to form a precipitate, which was removed. To the remaining supernatant, the organic solvent was further added (to a final organic solvent concentration of 90% V/V) and the mixture was kept at a low temperature (0°-10° C.) to effect complete precipitation of insoluble materials. The precipitate was collected, and dissolved in deionized water.

The resulting solution was passed through a column of a polysaccharide type anion exchanger, such as DEAE cellulose, CEAE Sephadex, or DEAE Sepharose pre-equilibrated with tris-HCl buffer (pH 6.5-8.5) with an ionic strength of 0.005-0.5. Elution was effected at pH 7.0-7.8 with the tris-HCl buffer with increased NaCl concentration. The eluate was subjected to gel filtration chromatography using Sephadex, Biogel or Ultrogel, preferably Sephadex G-75. More slowly eluted fractions (containing substances of M.W. 20,000-30,000) were collected and, if desired after ion exchange chromatography on CM-Sepharose, CM-Sephadex and the like, which are polysaccharide type cation exchangers, freeze-dried to yield the substance of the present invention.

The new α-amylase inhibitor of the present invention WAI-53, have the following characteristics 1) to 9):

(1) Being soluble in water or dilute salt solutions and insoluble in an organic solvent such as methanol, ethanol, acetone, chloroform and hexane.

(2) Having ultraviolet absorption maximum at 279 nm with $E_{1\%}^{279}$ being 12.8 in water (1 cm).

(3) Having molecular weight of 23,000-23,800 according to ultracentrifuge or 24,000 according to gel filtration.

(4) Giving a single band at an electrophoretic mobility of 0.53 on polyacrylamide gel electrophoresis according to the method described by Davis [Annals New York Academy of Science, 121, 404-427 (1964)]

(5) Giving a single band at an electrophoretic mobility of 0.60 when, after reduction with 2-mercaptoethanol in 6M urea and then carboxymethylation with monoiodo-acetic acid, subjected to electrophoresis according to the method of Davis using 6M urea-containing medium.

(6) Giving a single band on SDS polyacrylamide gel electrophoresis by the method described by Orth et al (Cereal Chemistry, 50, 190-7 (1973)) at the location corresponding to M.W. 13,000.

(7) Having serine at the N-terminal when analyzed by the method of Iwanaga et al [Protein, Nucleic acid, Enzyme, 15, 1037-54 (1970) in Japanese], with indicating the existence of two identical subunits.

(8) Being protein in nature with amino acid composition given below (taking isoleucine content being 2.33):
Lysine 4.55
Histidine 1.11
Arginine 7.66
Asparatic acid 6.97
Threonine 3.42
Serine 6.94
Glutamic acid 11.48
Proline 7.71
Glycine 9.41
Alanine 12.08
Valine 7.95
Isoleucine 2.33
Leucine 8.18
Throsine 4.10
Phenylalanine 1.61
and (9) Producing saturation curves of WAI-53 with human salivary α-amylase and with human pancreatic α-amylase with a ratio of the amount of WAI-53 required to produce 50% inhibition of human salivary α-amylase to that of human pancreatic amylase above 1:250. (See FIG. 1).

As described above, the α-amylase inhibitor according to the present invention is a new protein with the above specified molecular weight and electrophoretic characteristics.

The inhibitory activity of the α-amylase inhibitor of the present invention (WAI-53) is quite specific to human salivary α-amylase; and it has far less effect on human pancreatic α-amylase. This profile of specificity of inhibitory reaction exerted by the α-amylase inhibitor of the present invention, i.e. high ratio of inhibitory effect of WAI-53 on human salivary α-amylase to that on human pancreatic α-amylase is observed over a wide range of enzyme concentration. Thus, this agent may provide a useful means for the discriminative analysis of α-amylase isozymes in body fluid or in various clinical samples.

O'Donnell el al describes an isolation of an α-amylase inhibitor from wheat with inhibitory effect on human salivary α-amylase more pronounced than that on pancreatic α-amylase. They also suggest a possible method of discriminative analysis of α-amylase isozymes in clinical samples by the use of their α-amylase inhibitor [Clinical Chemistry 23, 560-566 (1977)].

However, the α-amylase inhibitor of O'Donnell et al has different electrophoretic mobility of 0.20 (in contrast to 0.53 of the present α-amylase inhibitor). And the α-amylase inhibitor described by O'Donnell et al has a ratio of specific inhibitory activities on each of the two human α-amylase isozymes smaller than that of the α-amylase inhibitor according to the present invention, and is accordingly not suitable for the discriminative analysis of α-amylase isozymes; the ratio of specific activities to produce 50% inhibition of the two α-amylase isozymes is not more than 100 for O'Donnell's inhibitor, while it is in a range of 200-300 for the inhibitor of the present invention. For example, as shown in FIG. 1, as little as 0.3 μg of the α-amylase inhibitor of the present invention is sufficient to produce 50% inhibition of the activity of 15 UI salivary α-amylase, whereas about 70-80 μg thereof is required to give 50% inhibition of the activity of 15 IU pancreatic α-amylase.

When the α-amylase inhibitor of the present invention is added to a mixture of human salivary α-amylase and pancreatic α-amylase of various ratios, the α-amylase inhibitor specifically inhibited the activity of the salivary α-amylase, and thus, the α-amylase activity of the mixture is found to correlate highly with the content of pancreatic α-amylase contained in the mixture.

Thus, the present invention provides a useful and simple method for the discriminative analysis of α-amylase isozymes.

The following examples describe a process for the preparation of the α-amylase inhibitor of the present invention and the use thereof in detail.

EXAMPLE 1

9 l. of purified water was added to 3 kg of wheat flour. The mixture was gently stirred for 1 hr and then centrifuged. Resulting 7 l. of supernatant was concentrated to 500 ml, and kept at 70° C. for 30 min. Resulting insoluble precipitate was removed by centrifugation. Addition of absolute ethanol to the clear supernatant to give final concentration of ethanol of 60% (V/V) at 4° C. produced some precipitate, which was removed by centrifugation. Absolute ethanol was further added to the resulting clear supernatant to give 90% (V/V) concentration of ethanol and the mixture was left overnight. The resulting precipitate was collected by centrifugation, washed twice with 99% ethanol and dried at room temperature under reduced pressure. Twenty three grams of crude α-amylase inhibitor was obtained.

The thus obtained crude dry solid product was dissolved in 0.02M tris-HCl buffer (pH 8.0) at 10% concentration, and the mixture was passed through a column containing 8.5 l. of DEAE Cepharose resin to effect adsorption thereof on the resin. The column was first washed with 17 l. of 0.05M tris-HCl buffer (pH 7.1) and then elution was performed using the same buffer solution and NaCl (0.0M-0.2M) gradient elution technique to give 10.2 l. of eluate, which was concentrated under reduced pressure to yield 75 ml of α-amylase inhibitor-containing solution. The resulting solution was subjected to Sephadex G-75 column chromatography using 0.05M acetate buffer (pH 5.0) to give 414 ml of solution containing the active α-amylase inhibitor. The solution was then further passed through a CM-Cepharose column. The column was first washed with 1.5 l. of 0.05M acetate buffer (pH 5.0). Then elution was performed with the same buffer solution using NaCl gradient elution technique (0.0M-0.3M) to give an active fraction, which was concentrated under reduced pressure to 31 ml. Desalting of the resulting concentrate with Sephadex G-25 gel filtration chromatography gave 609 ml of protein solution, which was freeze-dried to yield 20 mg of dry solid product, the new α-amylase inhibitor of the present invention (WAI-53) having the M.W. and electrophoretic characteristics described above.

The ratio of the amount of thus obtained α-amylase inhibitor (WAI-53) necessary to give 50% inhibition of human salivary α-amylase to that of human pancreatic α-amylase was approximately 1:250. Its specific α-amylase-inhibiting activity was 15 AIU/mg protein.

EXAMPLE 2

One mg of the α-amylase inhibitor (WAI-53) obtained in Example 1 was dissolved in 10 ml of 10mM tris-HCl buffer (pH 8.0) containing 10 mM of NaCl (Test solution A).

Purified human salivary α-amylase (S-AMY) and purified human pancreatic α-amylase (P-AMY) were each made to 100 u/l solution with 50mM phosphate buffer (pH 7.0), containing 50mM NaCl and 0.5mM $CaCl_2$ supplemented with 5% bovine serum albumin (fraction V). The thus prepared P-AMY and S-AMY solutions were mixed at various ratios as shown in Table 1 to give a number of 30 μl sample solutions.

TABLE 1

| Sample No. | 1 | 2 | 3 | 4 | 5 | 6 | 7 | 8 | 9 |
|---|---|---|---|---|---|---|---|---|---|
| S-AMY | 10 | 10 | 10 | 10 | 10 | 5 | 2 | 1 | 0 |
| P-AMY | 0 | 1 | 2 | 5 | 10 | 10 | 10 | 10 | 10 |
| P-AMY/S-AMY | — | 0.1 | 0.2 | 0.5 | 1 | 2 | 5 | 10 | — |
| P-AMY/P-AMY + S-AMY | 0.0 | 0.091 | 0.167 | 0.333 | 0.5 | 0.667 | 0.833 | 0.909 | 1.0 |

Each of 30 μl of the sample solution Nos. 1-9 was mixed with 10 μl of test solution A and the mixture was left at room temperature for 30 minutes (pre-incubation). Then α-amylase activity of the mixture was measured on an automatic analyzer (Model ABA-100, manufactured by Abbot Co.), using an α-amylase-test kit (manufactured and sold by Daiichi Kagaku Co., Ltd.)>Control mixture contained 10 μl of purified water instead of the test solution A.

Figure 2:
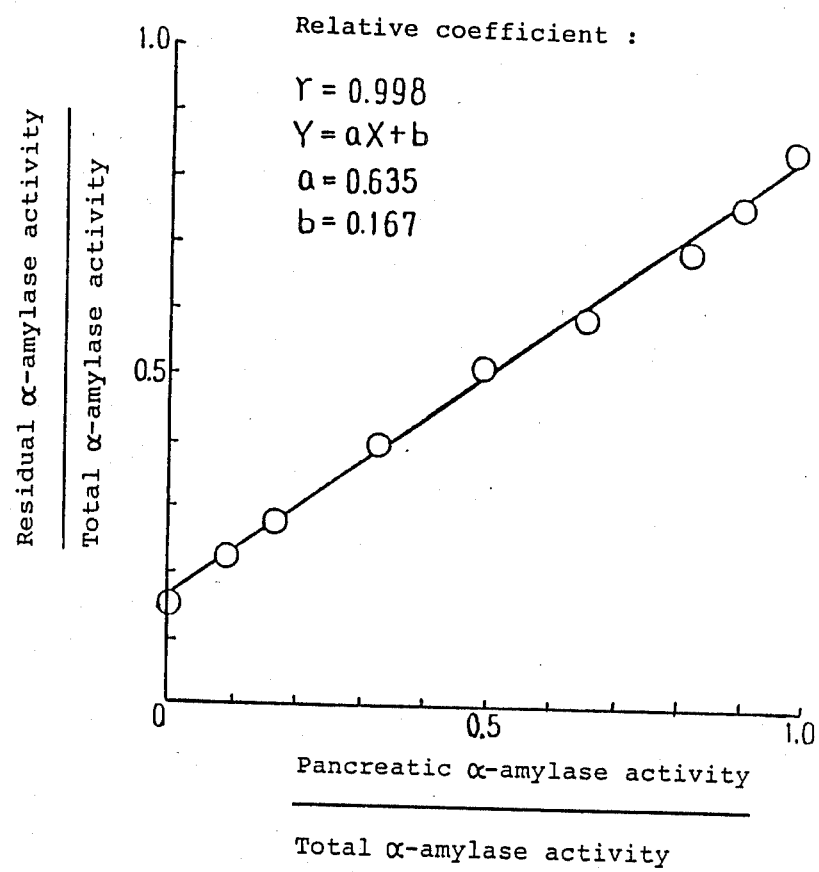
FIG. 2 shows a calibration curve of pancreatic α-amylase, useful for the discriminative α-amylase isozyme assay according to the present invention.

The thus obtained calibration curves for the discriminative analysis of α-amylase isozymes, P-AMY and S-AMY (FIG. 2) were used for the discriminative analysis of α-amylase isozymes in human serum samples.

Thirty μl each of 11 human serum samples was mixed with 10 μl of the test solution A. The mixtures were pre-incubated at room temperature for 30 minutes and then subjected to α-amylase activity assay described above. Mixtures of 30 μl each of the serum samples and 10 μl of purified water were used as control. The results are as given in Table 2.

TABLE 2

| Serum samples | % of pancreatic α-amylase isozyme by electrophoresis (x) | % of pancreatic α-amylase isozyme by present method (y) | Total α-amylase activity (enzymatic method) |
|---|---|---|---|
| 1 | 41 | 41 | 84 |
| 2 | 30 | 33 | 173 |
| 3 | 39 | 36 | 78 |
| 4 | 33 | 32 | 80 |
| 5 | 48 | 43 | 215 |
| 6 | 23 | 31 | 245 |
| 7 | 35 | 37 | 202 |
| 8 | 38 | 35 | 194 |
| 9 | 28 | 26 | 143 |
| 10 | 5 | 7 | 111 |
| 11 | 43 | 41 | 123 |

As shown above, the method of α-amylase analysis according to the present invention using the new α-amylase inhibitor of the present invention allows discriminative analysis of α-amylase isozymes in a more simple and quicker way than the conventional electrophoretic method described in [Rinsho-Kagaku, 5, 118 (1976) (in Japanese)].

What we claim is:

1. An α-amylase inhibitor, WAI-53, from wheat having the following properties:
   (a) being soluble in water or dilute salt solutions and insoluble in methanol, ethanol, acetone, chloroform and hexane;
   (b) having ultraviolet absorption maximum at 279 nm with $E_1\%$ 279 being 12.8 in water (1 cm);
   (c) having molecular weight of 23,000–23,000 according to ultracentrifugation or 24,000 according to gel filtration;
   (d) giving a single band at an electrophoretic mobility of 0.53 on polyacrylamide disc gel electrophoresis;
   (e) giving a single band at an electrophoretic mobility of 0.60 when, after reduction with 2-mercaptoethanol in 6 M urea and then carboxymethylation with mono-iodo-acetic acid, subjected to disc gel electrophoresis using 6 M urea-containing medium;
   (f) giving a single band on SDS polyacrylamide gel electrophoresis at the location corresponding to M.W. 13,000;
   (g) having serine at the N-terminus indicating the existence of two identical subunits;
   (h) being protein in nature with the amino acid composition:
   Lysine 4.55
   Histidine 1.11
   Arginine 7.66
   Aspartic acid 6.97
   Threonine 3.42
   Serine 6.94
   Glutamic acid 11.48
   Proline 7.71
   Glycine 9.41
   Alanine 12.08
   Valine 7.95
   Isoleucine 2.33
   Leucine 8.18
   Tyrosine 4.10
   Phenylalanine 1.61
   and
   (i) producing saturation curves of WAI-53 with human salivery α-amylase and of WAI-53 with human pancreatic α-amylase with a ratio of the amount of WAI-53 required to produce 50% inhibition of human salivary α-amylase to that of human pancreatic amylase above 1:250.

2. A process for the preparation of the α-amylase inhibitor, WAI-53, from wheat having the following properties:
   (a) being soluble in water or dilute salt solutions and insoluble in methanol, ethanol, acetone, chloroform and hexane;
   (b) having ultraviolet absorption maximum at 279 nm with $E_1\%$ 279 being 12.8 in water (1 cm);
   (c) having molecular weight of 23,000–23,000 according to ultracentrifugation or 24,000 according to gel filtration;
   (d) giving a single band at an electrophoretic mobility of 0.53 on polyacrylamide disc gel electrophoresis;
   (e) giving a single band at an electrophoretic mobility of 0.60 when, after reduction with 2-mercaptoethanol in 6 M urea and then carboxymethylation with mono-iodo-acetic acid, subjected to disc gel electrophoresis using 6M urea-containing medium;
   (f) giving a single band on SDS polyacrylamide gel electrophoresis at the location corresponding to M.W. 13,000;

(g) having serine at the N-terminus indicating the existence of two identical subunits;
(h) being protein in nature with the amino acid composition:
Lysine 4.55
Histidine 1.11
Arginine 7.66
Aspartic acid 6.97
Threonine 3.42
Serine 6.94
Glutamic acid 11.48
Proline 7.71
Glycine 9.41
Alanine 12.08
Valine 7.95
Isoleucine 2.33
Leucine 8.18
Tyrosein 4.10
Phenylalanine 1.61
and
(i) producing saturation curves of WAI-53 with human salivary α-amylase and of WAI-53 with human pancreatic α-amylase with a ratio of the amount of WAI-53 required to produce 50% inhibition of human salivary α-amylase to that of human pancreatic amylase above 1:250;

comprising: heating the supernatant of an aqueous extract from wheat or wheat flour, removing precipitate produced by fractional precipitation, adding aqueous acetone, ethanol or methanol giving an organic solvent concentration of 40–70%, collecting the precipitate produced by the addition of said organic solvent to 90% organic solvent concentration, dissolving the collected precipitate in water or salt solution, passing the solution through a polysaccharide type anion exchanger pre-equilibrated with tris-HCl buffer of pH 6.5–8.5 with an ionic strength of 0.005–0.5, eluting the absorbed material with tris-HCl buffer pH 7.0–7.8 with increased salt concentration by the addition of NaCl, subjecting the eluate to gel filtration chromatography and collecting more slowly eluting fractions corresponding to M.W. 20,000–30,000.

3. The method of claim 2 further comprising treating the eluate containing the 20,000–30,000 M.W. fractions with a polysaccharide type carbon exchanger and freeze-drying the resulting product.

4. A composition useful for the fractional quantitative analysis of α-amylase isozymes, comprising as the active component, the α-amylase inhibitor as defined in claim 1 in a carrier.

* * * * *

UNITED STATES PATENT AND TRADEMARK OFFICE
CERTIFICATE OF CORRECTION

PATENT NO. : 4,806,626

DATED : February 21, 1989

INVENTOR(S) : Koji Maeda and Osamu Oka

It is certified that error appears in the above-identified patent and that said Letters Patent is hereby corrected as shown below:

Claims 1 and 2, subparagraph (c) line 1, delete "23,000" second occurrence, insert -- 23,800 --.

Claim 2, subparagraph (h), line 20, delete "Tyrosein", insert -- Tyrosine --.

Signed and Sealed this

Twenty-seventh Day of February, 1990

*Attest:*

JEFFREY M. SAMUELS

*Attesting Officer*     *Acting Commissioner of Patents and Trademarks*